United States Patent
Yum et al.

(10) Patent No.: US 6,251,083 B1
(45) Date of Patent: Jun. 26, 2001

(54) INTERSTITIAL FLUID METHODS AND DEVICES FOR DETERMINATION OF AN ANALYTE IN THE BODY

(75) Inventors: Su I. Yum, Los Altos; Jeffrey N. Roe, San Ramon; Joel S. Douglas, Los Altos Hills, all of CA (US)

(73) Assignee: Amira Medical, Scotts Valley, CA (US)

( * ) Notice: Subject to any disclaimer, the term of this patent is extended or adjusted under 35 U.S.C. 154(b) by 0 days.

(21) Appl. No.: 09/391,002

(22) Filed: Sep. 7, 1999

(51) Int. Cl.[7] ........................................................ A61B 5/00
(52) U.S. Cl. ............................................. 600/584; 600/309
(58) Field of Search ...................... 600/309, 362, 600/365, 366, 367, 573, 584; 435/4

(56) References Cited

U.S. PATENT DOCUMENTS

| | | |
|---|---|---|
| 3,964,482 | 6/1976 | Gerstel et al. ............... 604/890.1 |
| 3,964,871 | 6/1976 | Hochstrasser ...................... 435/10 |
| 4,235,234 | 11/1980 | Whitney et al. ...................... 604/117 |
| 4,247,631 | 1/1981 | Nix et al. .......................... 435/10 |
| 4,270,920 | 6/1981 | Kondo et al. ....................... 23/230 B |
| 4,821,733 | * 4/1989 | Peck ............................... 600/361 |
| 5,139,023 | 8/1992 | Stanley et al. ..................... 600/368 |
| 5,140,985 | 8/1992 | Schroeder et al. .................. 600/323 |
| 5,161,532 | * 11/1992 | Joseph .............................. 600/345 |
| 5,250,023 | 10/1993 | Lee et al. ........................... 604/20 |
| 5,305,746 | 4/1994 | Fendrock ............................ 600/391 |
| 5,312,456 | 5/1994 | Reed et al. ......................... 411/456 |
| 5,421,816 | 6/1995 | Lipkover ............................ 604/20 |
| 5,443,080 | * 8/1995 | D'Angelo et al. .................... 600/573 |
| 5,458,140 | 10/1995 | Eppstein et al. .................... 600/573 |
| 5,586,553 | 12/1996 | Halili et al. ......................... 600/316 |
| 5,617,851 | 4/1997 | Lipkover ............................. 600/573 |
| 5,817,012 | * 10/1998 | Schoendorfer ...................... 600/362 |
| 5,890,489 | * 4/1999 | Elden ................................ 600/547 |
| 5,899,856 | * 5/1999 | Schoendorfer et al. ............. 600/362 |
| 5,962,215 | * 10/1999 | Douglas et al. ..................... 435/4 |
| 6,063,029 | * 5/2000 | Saita et al. .......................... 600/309 |
| 6,083,196 | * 7/2000 | Trautman et al. ................... 600/556 |

FOREIGN PATENT DOCUMENTS

| | | |
|---|---|---|
| WO 86/04680 | 8/1986 | (WO) . |
| WO 90/15568 | 12/1990 | (WO) . |
| WO95/02357 | 1/1995 | (WO) . |
| WO96/37155 | 11/1996 | (WO) . |
| WO96/37256 | 11/1996 | (WO) . |
| WO 97/30628 | 8/1997 | (WO) . |
| WO97/48440 | 12/1997 | (WO) . |
| WO97/48442 | 12/1997 | (WO) . |
| WO 98/34541 | 8/1998 | (WO) . |

* cited by examiner

*Primary Examiner*—John P. Lacyk
*Assistant Examiner*—Charles Marmor, II
(74) *Attorney, Agent, or Firm*—Burns, Doane, Swecker & Mathis, L.L.P.

(57) ABSTRACT

Devices and methods for utilizing dry chemistry dye indicator systems for body fluid analysis, such as glucose level provided by incorporating a porous membrane in a disposable patch. The devices also provide for microtitration of fluid samples in fixed volumetric openings containing indicator reagent. The devices provided are low cost due to efficient manufacturing methods provided.

61 Claims, 5 Drawing Sheets

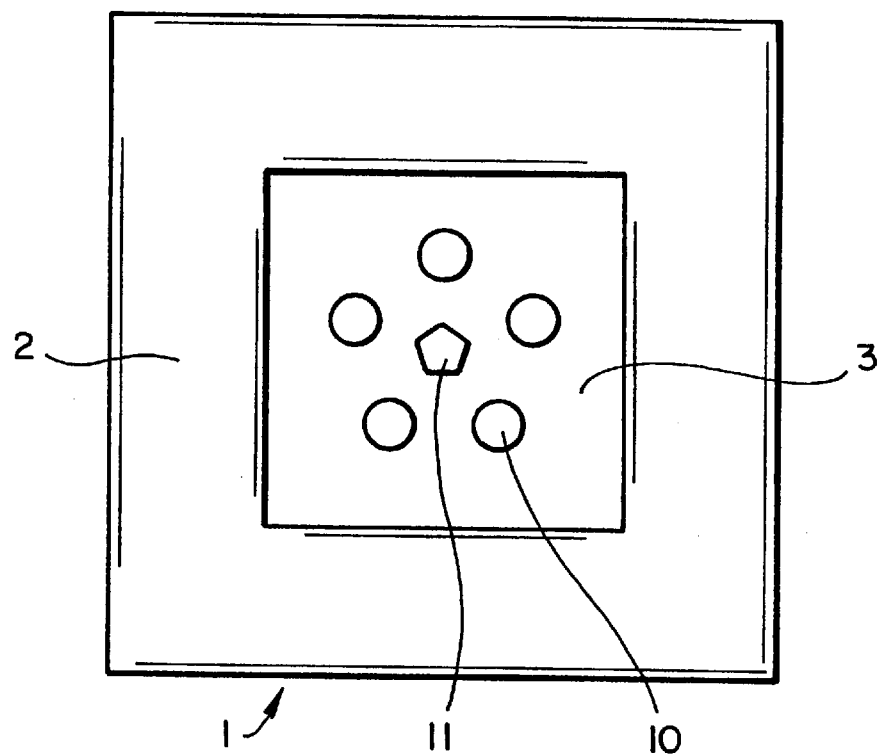
FIG_1
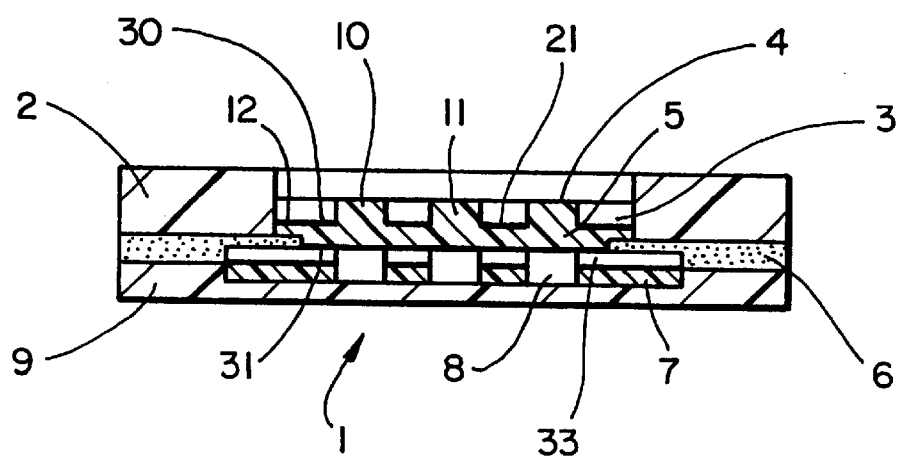
FIG_2

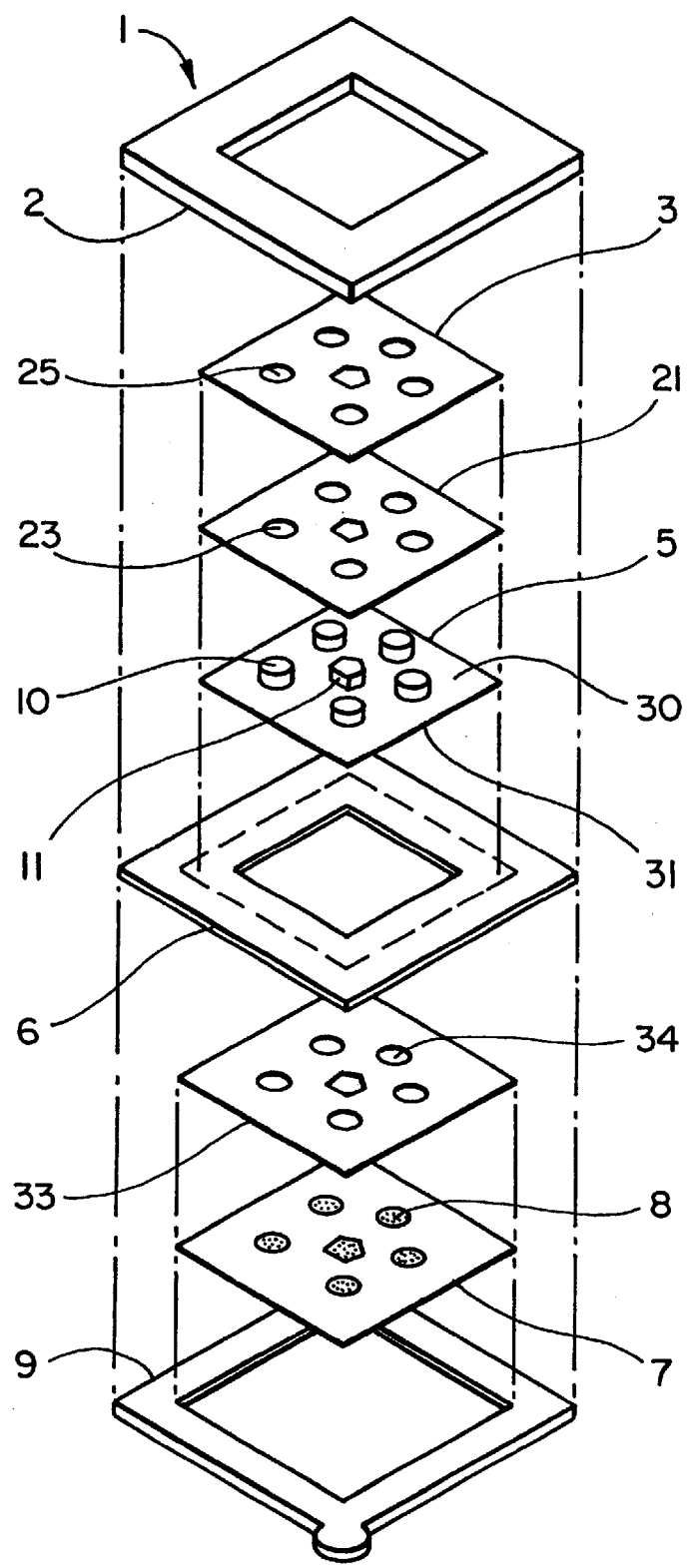
FIG_3

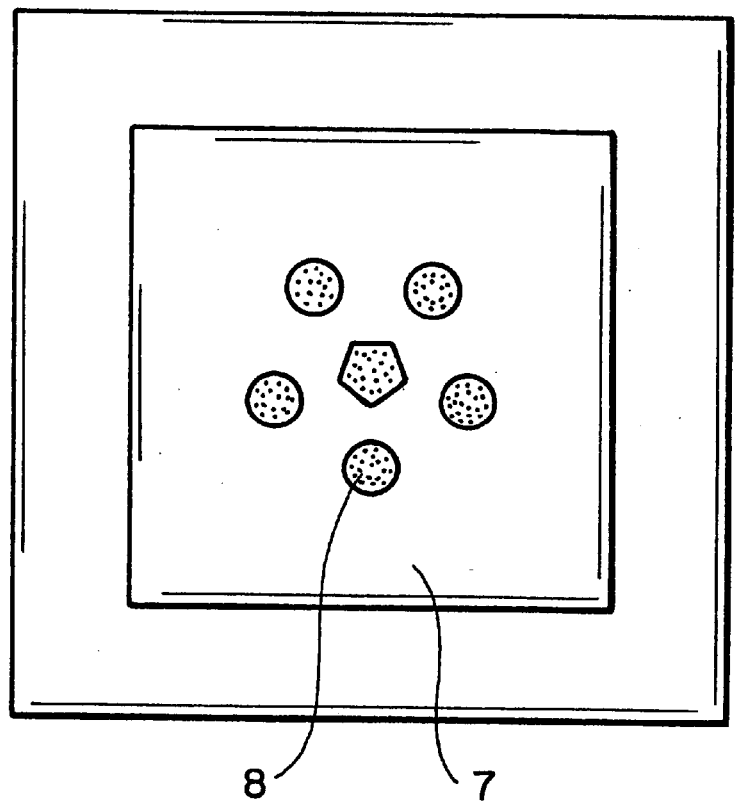
FIG_4
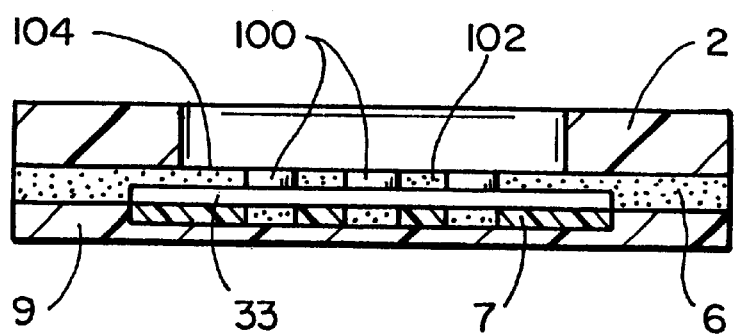
FIG_5

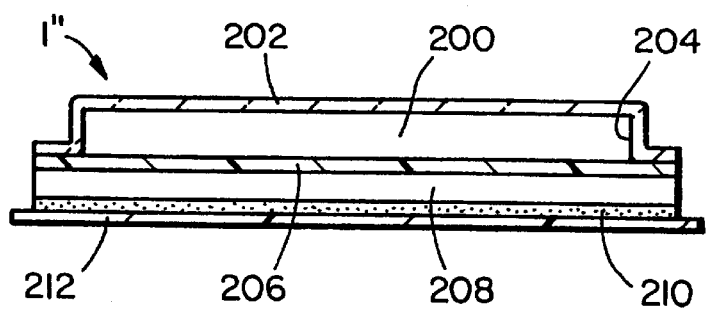
FIG_6
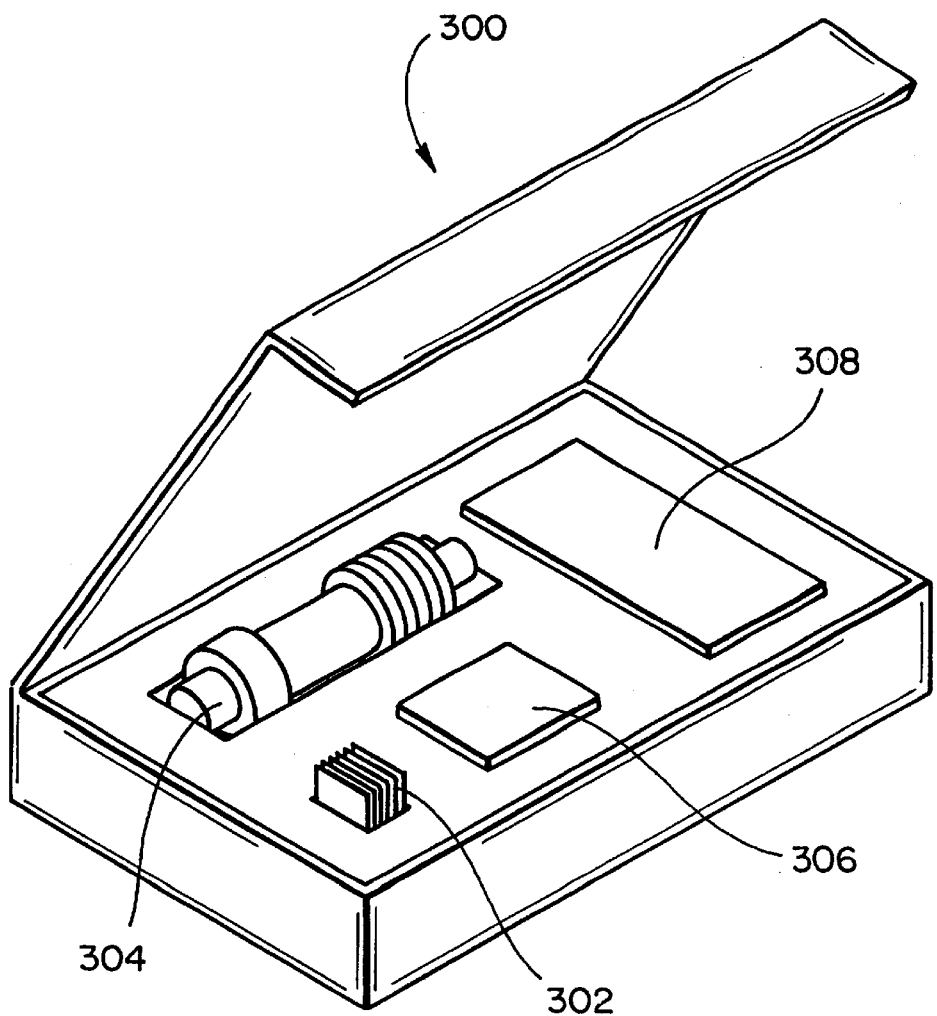
FIG_8

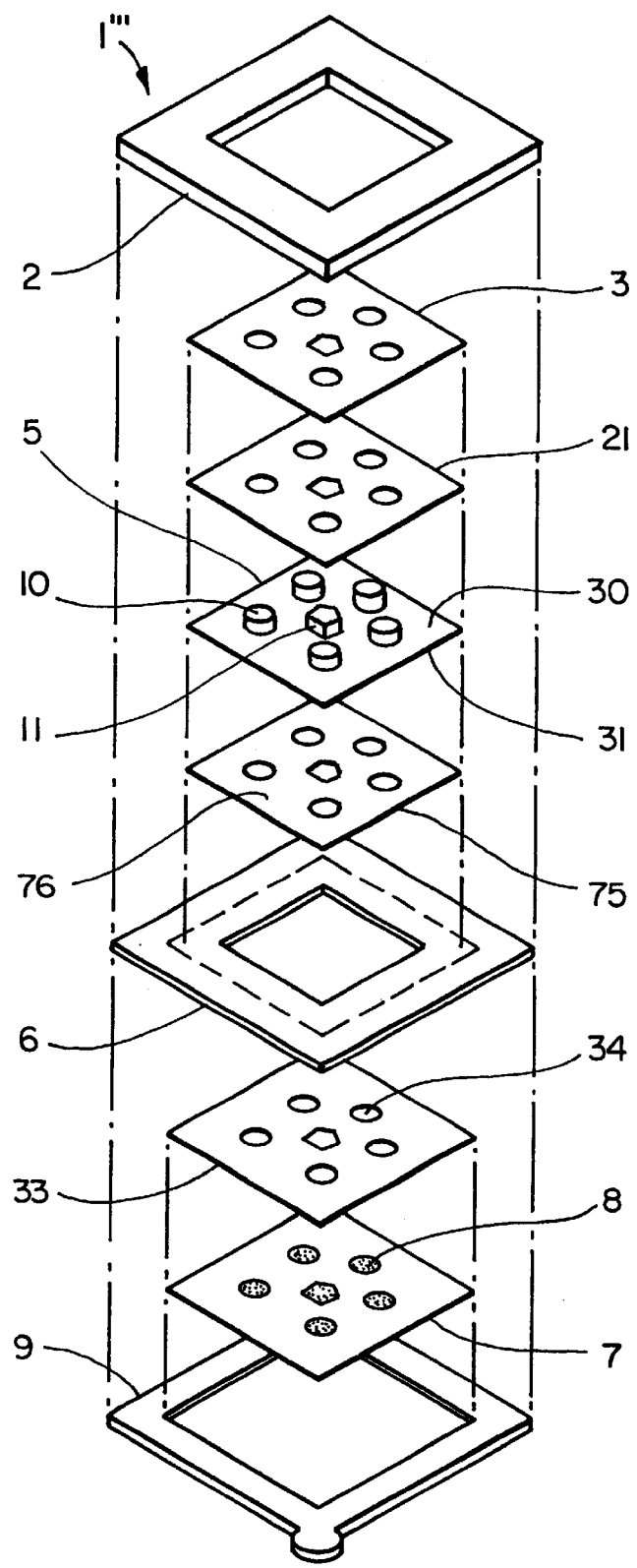
FIG_7

INTERSTITIAL FLUID METHODS AND DEVICES FOR DETERMINATION OF AN ANALYTE IN THE BODY

BACKGROUND

The present invention relates to a test device and method for the colorimetric determination of a chemical or biochemical component (analyte) in interstitial body fluid. In particular the present invention relates to a dry reagent test strip from which an analyte presence and/or concentration is determined by visual interpretation or by the use of an instrument. Such test strips are commonly used for determination of glucose level in blood by diabetics.

In the description of the Background of the present invention that follows, reference is made to ceratin structures and methods, however, such references should not necessarily be construed as an admission that these structures and methods qualify as prior art under the applicable statutory provisions. Applicants reserve the right to demonstrate that any of the referenced subject matter does not constitute prior art with respect to the present invention.

Numerous devices have been developed to test for presence and quantity of analytes in aqueous samples, such as whole blood or urine. The patent and technical literature of the last thirty years is replete with inventions which utilize a reagent strip containing a dry chemistry reagent system. A dry chemistry reagent system is a system in which the wet chemistries are imbibed into an absorbent or bibulous medium, dried, and later reconstituted by fluid from the test sample. The reagent strips contain an indicator which changes color, depending on the presence or concentration of a particular analyte in a biological fluid applied to the strip. These strips may be read visually by reference to a color standard or colorimetrically by an instrument calibrated or programmed to detect a certain color. Although some of these strips use reduction chemistries, more commonly they involve an oxidizable dye or dye couple. Some of the strips include an enzyme, such as glucose oxidase, which is capable of oxidizing glucose to gluconic acid and hydrogen peroxide. They also contain an oxidizable dye and a substance having peroxidative activity, which is capable of selectively catalyzing oxidation of the oxidizable dye in the presence of hydrogen peroxide. (See, for example, U.S. Pat. No. 5,306,623, to Kiser et al.). Examples of these devices, in addition to those used to test blood glucose, include tests for cholesterol, triglycerides, calcium or albumin in whole blood, and for protein, ketones, albumin or glucose in urine.

Dry chemistry reagent strips incorporating enzyme-based compositions are used daily by millions of diabetics to determine blood glucose concentrations. The NIH sponsored study, the Diabetes Complications and Control Trial, demonstrated conclusively that careful control of blood glucose levels can significantly reduce the incidence of serious complications of diabetes such as vision loss and kidney malfunction. Most diabetics must test themselves periodically in order to make appropriate adjustments to their diet or medication. It is thus especially important for diabetics to have rapid, low pain, and accurate reagent strips for glucose determination. The embodiment of dry chemistry reagent systems in test strips enable simple yet effective analytical protocols. However, current blood base devices require the patient to lance their fingers with a lancing device which cause considerable initial and residual pain. This process has caused many patients to reduce the amount of testing they do because of the pain associated with testing.

The technologies embodied in the products which have been developed to date have certain limitations from the perspective of the end user and/or the manufacturer. The issues surrounding sample acquisition and the complexities of measuring in or separating blood are a significant issue for the current technology. The existing technology to acquire a blood sample utilizes fingersticks which hurt. U.S. Pat. No. 5,951,492, entitled "Methods and Apparatus for Sampling and Analyzing Body Fluid", describes a means for painless blood sampling. This system still requires needles and blood and a mechanism or device for blood sampling. Blood is plentiful but hard to read calorimetrically due to red cell presence. There is, therefore, a need to overcome some of the limitations of currently available colormetric testing systems. U.S. Pat. No. 3,092,465, issued to Adams et al., U.S. Pat. No. 3,298,789, issued to Mast and U.S. Pat. No. 3,630,957, issued to Rey et al., all describe a basic reagent system which became a standard for calorimetric determination of glucose in biological samples. These patents describe the formation of a film layer or semi-permeable coating over the bibulous matrix to hold back the larger particulates, such as red blood cells, and allow fluid to permeate into the bibulous matrix. This approach requires the removal of red blood cells by washing or wiping to enable visual inspection or instrument reading of the indication of the dye color formed in the matrix.

U.S. Pat. No. 3,607,093 to Stone, discloses a membrane for testing blood where the membrane has a skin permeable to solutions but impermeable to solids such as red blood cells and to macromolecules such as proteins. This membrane is disclosed as being used by applying a blood sample then wiping away the red blood cells from the skin in order to reach the test indication through the skin.

U.S. Pat. No. 3,552,928, issued to Fetter, discloses the use of certain water soluble salts and amino acids in reagent formulations as separation agents to provide blood separation. With solids such as red blood cells substantially removed from the biological fluid, there is less background color at the test site to obscure a change in coloration produced by a testing reagent.

Phillips et al., U.S. Pat. No. 4,935,346, discloses a system wherein a whole blood sample is applied to the device and indicator development occurs in the presence of the colored components of the sample. Measurements of the color change in indicator are made at two distinct wavelengths to eliminate the interferences from the presence of colored blood components.

Kiser et al., U.S. Pat. Nos. 5,306,623 and 5,418,142, disclose a visual meter device which incorporates various coatings on a matrix material to filter red blood cells from fluids. Similar devices for visual indication are disclosed by Hochstrasser in U.S. Pat. Nos. 3,964,871 and 4,059,407.

Terminello et al., U.S. Pat. No. 4,774,192, disclose a system in which the matrix is formed of an asymmetric material used to filter the red blood cells in the sample. The asymmetric material has a density gradient from one side to the other to progressively separate red blood cells from the fluids.

Daffem et al., U.S. Pat. No. 4,994,238, disclose a test device that comprises an asymmetric reagent layer that has progressively finer filtration with increased distance from one surface toward the other surface.

Castino et al., U.S. Pat. No. 5,456,835, disclose the use of filters formed of ligand modified polymeric film such as polypropylene fibers and polyethersulfone fibers.

Vogel et. al., U.S. Pat. No. 4,477,575, disclose the use of glass fiber material to achieve blood separation through the thickness of the material. Blood is applied to one side of the glass fiber, and relatively clear fluid migrates out of the opposite side. This fluid is delivered to an additional layer where the detection of analytes can occur.

Macho et al., U.S. Pat. No. 5,451,350, disclose the use of absorbent channels to distribute sample fluid in multi-zone test devices. Charlton et al., U.S. Pat. No. 5,208,163, also disclose the use of capillary channels to distribute blood to various chambers in the device.

In order to avoid the pain and/or complexity of measuring in whole blood, some people have sought to access interstitial fluid. The professed advantages are painlessness and bloodlessness (consumer and measurement system advantages). Many of these approaches leverage approaches designed to deliver drugs to the interstitial space in lieu of needle injections or other means of drug delivery. Others have pursued noninvasive approaches to analyte measurement.

Gerstel et al., U.S. Pat. No. 3,964,482, disclose the use of a drug delivery device for precutaneous administration of a drug comprising of a plurality of projections.

Japanese Patent No. JP 2551743-B2 assigned to Sansei Denki KK describes a skin damage forming device for medicine delivery. This device causes small holes formed by tiny needles in the device.

Fendrock, U.S. Pat. No. 5,305,746, describes a patch for reducing skin impedance by using an array of flexible tines.

Whitney et al., U.S. Pat. No. 4,235,234, discloses a subcutaneous injection system which uses projections to inject a drug into the tissue.

Azimi, World Patent WO 95/02357, discloses a noninvasive glucose monitor that does not rely on heat, electricity or chemicals to collect glucose from interstitial fluid across a patient's skin.

Liplovker, U.S. Pat. No. 5,617,851, discloses a noninvasive method and apparatus for withdrawing fluid from an organism and determining the concentration of a substance in the fluid.

Liplovker, U.S. Pat. No. 5,421,816, discloses a method of using ultrasound to move a drug across the skin of a patient.

Halili et al., U.S. Pat. No. 5,586,553, discloses a transcutaneous sensor placed at a selected site within a patient's body to determine the concentration of analyte in a patient.

Eppstein et al., U.S. Pat. No. 5,458,140, discloses a method of enhancing the permeability of the skin using ultrasound either in the presence or absence of chemical skin permeation enhancers to permit analytes to cross the skin to an analyte collection site.

Schroeder et al., U.S. Pat. No. 5,140,985, discloses a device which measures the blood glucose of a patient via the concentration of glucose in sweat.

Stanley et al., U.S. Pat. No. 5,139,023, disclose an apparatus and method for noninvasive blood glucose monitoring by correlation with amount of glucose which permeates an epithelial membrane. The glucose receiving medium includes a glucose permeation enhancer capable of increasing the permeability of glucose across the epithelial membrane.

The disclosures of the above-discussed documents are incorporated herein by reference. The devices and methods discussed above provide varying degrees of effectiveness of blood analysis at varying degrees of complexity and pain.

It is an object of the present invention to provide improved devices and methods to improve the performance and minimize the pain and complexity compared to the prior art devices.

It is a further object of the present invention to provide a fully disposable, discrete reading system for detecting analyte presence or concentration.

It is another object of this invention to provide a dry reagent chemistry system capable of analyzing body fluids for one or more analytes without finger lancing.

It is another object of this invention to provide a means for performing microtitration for the analysis of body fluid in a system which enables the ready visual determination of analyte presence or concentration.

The above objects as well as others are achieved by the devices, methods and systems of this invention as disclosed herein.

SUMMARY OF THE DISCLOSURE

One aspect this invention provides a device for testing a body for the presence or concentration of an analyte, such as glucose.

The device can be described as a device for determining the presence or concentration of an analyte in the interstitial body fluid of a patient, the device comprising: (a) a plurality of test areas, each test area independently comprising (i) a porous matrix material having an absorption side and a test side and (ii) an indicating reagent system positioned on or impregnated in the test side of the porous matrix material, wherein each indicating reagent system is capable of indicating the presence or concentration of an analyte in interstitial body fluid by producing a spectrophotometric change upon contact with the interstitial body fluid; (b) a substantially non-porous material separating each test area from adjacent test areas; (c) an attachment means for attaching the device to the skin of a patient; and (d) an extraction means for extracting interstitial body fluid through the skin of the patient; wherein each test area is oriented so that the absorption side of the test area is positioned to contact the interstitial body fluid extracted through the skin of the patient.

Another aspect of the present invention includes a method for testing the interstitial body fluid of a patient for the presence or concentration of an analyte comprising: providing a device comprising (a) a plurality of test areas, each test area independently comprising (i) a porous matrix material having an absorption side and a test side and (ii) an indicating reagent system positioned on or impregnated in the test side of the porous matrix material, wherein each indicating reagent system is capable of indicating the presence or concentration of an analyte in interstitial body fluid by producing a spectrophotometric change upon contact with the interstitial body fluid; (b) a substantially non-porous material separating each test area from adjacent test areas; (c) an attachment means for attaching the device to the skin of a patient; and (d) an extraction means for extracting interstitial body fluid through the skin of the patient; wherein each test area is oriented so that the absorption side of the test area is positioned to contact the interstitial body fluid extracted through the skin of the patient;

attaching the device to the skin of a patient; extracting interstitial body fluid through the skin of the patient and onto the absorption side of the test areas; detecting or measuring a spectrophotometric change or the absence thereof on the test side of the test areas.

Another aspect of the present invention includes a process for preparing a device for determining the presence or concentration of an analyte in the interstitial body fluid of a patient, the device comprising: (a) a plurality of test areas, each test area independently comprising (i) a porous matrix material having an absorption side and a test side and (ii) an indicating reagent system positioned on or impregnated in the test side of the porous matrix material, wherein each indicating reagent system is capable of indicating the presence or concentration of an analyte in interstitial body fluid by producing a spectrophotometric change upon contact with the interstitial body fluid; (b) a substantially non-porous material separating each test area from adjacent test areas; (c) an attachment means for attaching the device to the skin of a patient; and (d) an extraction means for extracting interstitial body fluid through the skin of the patient; wherein each test area is oriented so that the absorption side of the test area is positioned to contact the interstitial body fluid extracted through the skin of the patient;

the process comprising the steps of:

providing a porous matrix material having an absorption side and a test side; applying an indicating reagent system to the test side of the porous matrix material, wherein the indicating reagent system is capable of indicating the presence or concentration of an analyte in interstitial body fluid by producing a spectrophotometric change upon contact with the interstitial body fluid; compressing a pre-determined portion of the porous matrix material to form a substantially non-porous compressed area and a plurality of uncompressed test areas, each test area comprising the porous matrix material having the indicating reagent system positioned on or impregnated in the test side of the material, the substantially non-porous compressed area being located between each test area; optionally applying a substantially non-porous material between each test area; applying or attaching an extraction means for extracting interstitial body fluid through the skin of a patient to the absorption side of the matrix material; applying or attaching an attachment means for attaching the device to the skin of the patient to the absorption side of the matrix material and/or to the extraction means to form the device.

Another aspect of the present invention includes a process for preparing a device for determining the presence or concentration of an analyte in the interstitial body fluid of a patient, the device comprising: (a) a plurality of test areas, each test area independently comprising (i) a porous matrix material having an absorption side and a test side and (ii) an indicating reagent system positioned on or impregnated in the test side of the porous matrix material, wherein each indicating reagent system is capable of indicating the presence or concentration of an analyte in interstitial body fluid by producing a spectrophotometric change upon contact with the interstitial body fluid; (b) a substantially non-porous material separating each test area from adjacent test areas; (c) an attachment means for attaching the device to the skin of a patient; and (d) an extraction means for extracting interstitial body fluid through the skin of the patient; wherein each test area is oriented so that the absorption side of the test area is positioned to contact the interstitial body fluid extracted through the skin of the patient;

the process comprising the steps of: providing a porous matrix material having an absorption side and a test side; compressing a pre-determined portion of the porous matrix material to form a substantially non-porous compressed area and a plurality of uncompressed test areas, each test area comprising the porous matrix material, the substantially non-porous compressed area being located between each test area; optionally applying a substantially non-porous material between each test area; applying an indicating reagent system to the test side of each test area, wherein each indicating reagent system is capable of indicating the presence or concentration of an analyte in interstitial body fluid by producing a spectrophotometric change upon contact with the interstitial body fluid; applying or attaching an extraction means for extracting interstitial body fluid through the skin of a patient to the absorption side of the matrix material; applying or attaching an attachment means for attaching the device to the skin of the patient to the absorption side of the matrix material and/or to the extraction means to form the device.

Yet another aspect of the present invention includes a kit for use by a patient to determine the presence or concentration of an analyte in the interstitial body fluid of the patient, the kit comprising: (1) a device comprising: (a) a plurality of test areas, each test area independently comprising (i) a porous matrix material having an absorption side and a test side and (ii) an indicating reagent system positioned on or impregnated in the test side of the porous matrix material, wherein each indicating reagent system is capable of indicating the presence or concentration of an analyte in interstitial body fluid by producing a spectrophotometric change upon contact with the interstitial body fluid; (b) a substantially non-porous material separating each test area from adjacent test areas; (c) an attachment means for attaching the device to the skin of a patient; and (d) an extraction means for extracting interstitial body fluid through the skin of the patient; wherein each test area is oriented so that the absorption side of the test area is positioned to contact the interstitial body fluid extracted through the skin of the patient; (2) an applicator means for positioning and placing the device on the skin of the patient.

Yet a further aspect of the present invention includes a device for determining the presence or concentration of an analyte in the interstitial body fluid of a patient, the device comprising: a substantially impermeable backing; a semipermeable membrane secured to the backing to form at least one pocket; a gel including an indicator reagent capable of indicating the presence of an analyte in interstitial body fluid by producing a spectrophotometric change upon contact with the interstitial body fluid; an absorption side matrix in communication with the semipermeable membrane; and an adhesive located on the absorption side of the matrix, the adhesive capable of securing a device to a patient.

The above sets forth the generic aspects of the various devices and methods of the present invention. A more detailed description of the invention is made below.

BRIEF DESCRIPTION OF THE DRAWINGS

FIG. 1 is a top plan view of a first embodiment of a patch in accordance with the present invention showing result indications in a matrix member;

FIG. 2 is a sectional view of the device shown in FIG. 1;

FIG. 3 is a perspective exploded view of the device shown in FIG. 1;

FIG. 4 shows a bottom plan view of the device shown in FIG. 1 showing the skin interface zones under each result indicator area;

FIG. 5 is a sectional view of a second embodiment of a patch in accordance with the present invention impregnated isolation and skin interface zones under each result indicator area;

FIG. 6 is a sectional view of a third embodiment of a patch in accordance to the present invention;

FIG. 7 is a perspective exploded view of a fourth embodiment of a patch according to the present invention; and FIG. 8 a perspective view of a kit according to the present invention.

DETAILED DESCRIPTION OF PREFERRED EMBODIMENTS

The devices of the present invention are simpler to use and are easier and less painful than most devices previously available. This is especially important for diabetics who rely on blood glucose testing multiple times per day to keep their disease under control. For many diabetics, the pain associated with blood glucose monitoring is prohibitive and prevents the patient from testing. Devices of various configurations and various uses based on the embodiments of the invention disclosed herein can be delivered to the diabetic and do not cause pain from finger tip lancing. The ease of use and portability of these devices, coupled with the painless operation of these devices will facilitate increased patient compliance with recommended testing routines and will result in improved overall health of diabetic patients.

As described further below, one or more aspects this invention uses an intrinsically hydrophilic membrane. The hydrophilic nature of the membrane encourages absorption of the sample, provides a suitable matrix for testing the sample and provides a substrate for applying the indicating reagent and subsequently drying it to the matrix fibers.

The invention can be used with various membranes including fiber, polyethersulfone, polyamide, and other polymeric membranes. However, membranes such as the Whatman 41 and Pall Gelman Sciences Supor 200 are preferable for this application.

The most preferred type of microporous membranes are polyethersulfone polymeric membrane (Pall Gelman Sciences Supor 200 is an example) which is formed with a microporous skin side which acts as a reflectance surface for the test side of the membrane and a matrix side which has uniform pore size for wicking in the sample. The membranes are treated with test reagents which are designed to react with the analyte being tested. However, membranes having a matrix layer having uniform porosity but no reflectance skin are also within the scope of this invention.

A second preferred type of membranes includes cellulose fiber or polymer based membranes or matrix products which facilitate wicking (Whatman 41 is an example). Membranes of the second type are preferably cellulose fiber or polymer based membranes and can also be treated with test reagents. During use, clear interstitial fluid moves from the absorbent side into the test zone and reacts with the indicator reagents to indicate the presence and concentration of analyte.

The test or reaction zones must be positioned such that clear interstitial fluid migrates into the zones and such that each reaction zone is isolated from other reaction zones. The reaction zones are isolated by either embossing the matrix to restrict the flow between zones or imbibing the area between zones with a hydrophobic barrier such as hot melt adhesive, or a silicone and fluorocarbon coating. These isolated zones are microtitration areas. Providing a uniform and adequate sample volume for the test or reaction zones assures a uniform test at each test site.

The invention provides different mechanisms for using the dry chemistry reagent systems with and without microtitration volume control. The dry chemistry components and microtitration principles are described below, independent of the embodiments which follow.

The microtitration concept employed in some aspects of this invention can be explained as a method of controlling the sample volume and the reagent amount to give a consistent titration and therefore consistent and reliable results. This concept is described in Douglas et al., WO 97/38126.

The first step is to create a test zone which is bounded. The traditional wet chemistry analysis uses a fixed (premeasured) volume of sample and titrates a quantity of test reagent against that sample. In a dry format the quantity of the test reagent has to be impregnated into the matrix in a ratio proportional to the void volume of the matrix. This can be accomplished many different ways known in the art. The sample volume (SV) is the void volume of the matrix (VVM) minus the solids volume of the test reagent remaining in the matrix, (TRV) from the test reagent following wet application and drying of the test reagent. Therefore, SV=VVM−TRV. The ratio SV/TRV must be constant to provide an accurate titration.

To achieve microtitration the material void volume and the reagent application must be controlled. The device of this invention creates a fixed control geometry which does not permit significant fluid flow between test zones and the sample delivery channel. The membrane has a tendency to wick laterally, which the device in this aspect of the invention prevents. The fluid is delivered so that it enters the test area matrix from the absorbent side of the matrix. The test reagent can either be applied to the matrix by the technique described in U.S. Pat. No. 5,547,702, issued to Gleisner, or by discretely applying it in the reaction zones. To discretely apply the reagent only in the reaction zones a syringe or needle is used to apply the reagents in the test area. The most effective way to do this is to preassemble the device and coat the reagents while the membrane is supported by the test device construction. The other materials can be impregnated into the matrix either locally or by a generally controlled application. The most preferred method is to apply the test reagent as described in U.S. Pat. No. 5,547,702. This system can be modified for discrete reagent application and is further elaborated in Douglas et al., U.S. Pat. No. 5,876,957, which is incorporated herein by reference.

In this invention, the preferred method for controlling the test area geometry is to emboss the membrane into the a gasket mask or molded part, deforming a portion of the membrane into openings in the gasket or molded part and leaving the test areas uncompressed and compressing a portion of the membrane. The compressed areas are preferably fastened to the gasket with an adhesive such as 3M grade 415 acrylic pressure sensitive adhesive, to create test areas which are completely bounded on the sides, thus preventing any flow between the test areas. In this way, the only entry into each opening is through the absorbent side of the matrix.

Preferably, the membrane is embossed into the gasket or mask by bringing both pieces together between two platens of a hydraulic press. A portion of the membrane is pushed into the gasket openings and deforms the material outside of the openings by compressing that material so that the thickness is reduced by 80% to 95% in the compressed area.

In one embodiment of the present invention, the embossed material can be die cut and the compressed area can be removed (in a process similar to creating a label on a printing press) to further eliminate any chance for crosstalk or flow between test zones. In this embodiment the test zones are held to the device by a small ring of adhesive because the majority of the embossed or compressed material has been removed. The adhesive seals the die-cut matrix inserts to the gasket member, thereby preventing any leakage of fluid between test zones or areas.

The indicating reagent mix must be capable of detecting the presence of the analyte. In general, the analyte reacts with a specific oxidase enzyme and produces hydrogen peroxide. This strongly oxidative substance reacts with the indicator(s) present to produce a colored end product. The oxidase enzyme may be one of the following: glucose oxidase, cholesterol oxidase, uricase, alcohol oxidase, aldehyde oxidase or glycerophosphate oxidase. While the examples and preferred embodiments herein comprise glucose oxidase in the formulations, formulation changes required to utilize other oxidase enzymes are evident to one who is skilled in the art.

The indicator chemistries which provide acceptable color generation when coated on the microporous membrane from Pall Gelman (polyethersulfone), or Whatman 41 cellulose fiber matrix include 3-methyl-2-benzothiazolinone hydrazone hydrachloride (MBTH) combined with 3,3-dimethylaminobenzoic acid (DMAB), MBTH combined with 3,5-dichloro-2-hydroxybenzene-sulfonic acid (DCHBS); 4-aminoantipyrene (4-AAP) (at 4 mg/ml) and 5-Oxo-I-(p-sulfophenyl)-2-pyrazoline-3-carboxylic acid (OPSP); 4-AAP (at 4 mg/ml) and n-(m-tolyl) diethanolamine (NDA); 2,2'-azino-di (3-ethylbenzthiazoline) sulfonic acid (ABTS); 4AAP (at 4 mg/ml) and 4-methoxynaphthol; pyrogallol red(PGR); bromopyrogallol red (BPR); acid green 25 (AG); MBTH and 8-anilino-1-naphthalenesulfonate (ANS); or N-(3-sulfopropyl)aniline and MBTH; or other known and conventional dye system for different analytes. U.S. Pat. No. 5,306,623 to Kiser et al., discloses effective concentrations of a number of useful dye systems.

A preferred dye system is disclosed in U.S. Pat. No. 5,776,719, which is incorporated herein by reference. Klose et al., U.S. Pat. No. 4,101,381, also describes a MBTH-S formulation. This preferred dye system is based on the sulfonated form of MBTH, 3-Methyl-6-(M sulfonate) benzothiazolinone-(2)-hydrazone (MBTH-S) where M is sodium, potassium, ammonium or other equivalent ion, but is preferably sodium. MBTH-S formed as a dye couple with DMAB, ANS or N-(3-sulfopropyl)aniline provides an indicator system which provides a stable color end point in a short period of time. This dye system enables visual reading on a reliable basis without the use of meters or complex timing sequences.

Certain indicators such as MBTH-DMAB continue to change color over time, i.e., the reaction does not reach a stable end point within a reasonable time period. When it is desirable that such an indicator dye system is used, it is important to take the desired readings at a specific time after wetting the test strip and beginning the reaction. U.S. Pat. No. 5,049,487 to Phillips et al., incorporated herein by reference, describes the use of a change in reflectance of the matrix as a signal that the matrix has been wetted by the sample.

The MBTH-ANS system described by Yu in U.S. Pat. No. 5,453,360, may be used in the methods and devices of this invention. However, both components require an acid pH of approximately 4.0, which is indicated enhances enzyme activity and requires the use of higher levels of oxidase or peroxidase enzymes than desired in the chemistry system. A near neutral pH system is more preferred. MBTH-S and ANS dye system referred to above can exist at approximately a pH of 6 and has the advantages of being easier to formulate and enhanced enzyme activity. MBTH-S coupled with ANS provides good spectral absorption, is water soluble and does not sublime under dry chemistry storage conditions. A preferred dye system of the MBTH-S and ANS dye couple can be used in the device of present invention because of the clear fluid absorbed into the reaction site provided by the devices and methods of present invention. The spectral absorption in the range of 580–650 nm of the dye system is acceptable due to the clear color of the absorbed fluid. This range produces colors which are purple to blue. One who is skilled in the art can formulate an acceptable chemistry based on the components disclosed herein and in the prior art.

The above reagents will create a chemistry which can be read with either a meter or by visual color comparison. To create a visual strip which can be read in binary fashion as described in U.S. Pat. No. 3,964,871, issued to Hochstrasser, a plurality of test areas must be designed into the test device. To permit the chemistry to be sensitive to threshold levels of analytes an antioxidant is used to inhibit or intercept the reaction in visual test zones which only change color if the analyte is present in a greater quantity than the inhibition chemistry in that zone. They participate in a noncompetitive reaction and are consumed first by the hydrogen peroxide. If the antioxidant is fully consumed by the reaction the dye indicator or indicators are oxidized and color is developed in the test matrix. Hochstrasser, U.S. Pat. No. 3,964,891, provides the background to the design and implementation of a urine inhibition test strip. Kiser et al., U.S. Pat. No. 5,306,623, expands this for blood testing. Antioxidants which can be utilized include 2,3,4-trihydroxybenzoic acid, propyl gallate, ascorbic acid, isoascorbic acid, 3,4 dihydroxy cinnamic acid, 3,4 dihydroxy benzaldehyde, Gallic acid and 5,6-diaminouracil. The antioxidant which is preferred in this embodiment is ascorbic acid.

Antioxidants may also be used to delay the onset of the desired reaction sequence. Another aspect of this invention is the use of antioxidants such as ascorbic acid to consume possible contaminants (such as intracellular fluid, which may be present upon penetrating the stratum corneum and which could dilute the interstitial fluid and analytes measured therein) before the preferred reaction sequence is triggered.

This can be achieved by designing the absorption system so that it is capable of absorbing a significant amount of fluid. This causes a dilution effect which can dampen out the issues associated with the contamination of the initial fluid absorbed by the device. The reaction is delayed by applying ascorbic acid or another antioxidant to the device in an amount sufficient to delay the conversion of the indicator (damping antioxidant). The antioxidant is used in the reaction to convert the glucose in the initial sample and as it is consumed the glucose found in the initial sample is no longer available to convert the indicator. The amount of antioxidant would be in addition to any antioxidant needed to create a multi-zone reading device. Kiser et al., in U.S. Pat. Nos. 5,306,623 and 5,418,142, disclose a visual meter device which incorporates the use of antioxidants. Similar devices for visual indication are disclosed by Hochstrasser in U.S. Pat. Nos. 3,964,871 and 4,059,407. However, the concept of using the antioxidant to delay the reaction and consume contaminated portion of a sample has not been developed in the prior art.

To insure adequate glucose sample (which contains the analyte to be measured), skin permeation enhancers such as those described in Stanley et al., U.S. Pat. No. 5,139,023, are used. The skin permeation enhancers include natural bile salt, sodium cholate, sodium dodecyl sulfate, sodium deoxycholate, taurodeoxycholate or sodium glycocholate. Various fatty acids can also be used as a skin permeation enhancers. The most preferred embodiment uses one or more combinations of skin permeation enhancers in conjunction with other mechanical means such as ultrasound, iontophoresis and tape stripping.

Such permeation enhancers can be selected from, but are not limited to $C_{2-4}$ alcohols such as ethanol and isopropanol, polyethylene glycol monolaurate, polyethylene glycol-3-lauramide, dimethyl lauramide, esters of fatty acids having from about 10 to about 20 carbon atoms, and monoglycerides or mixtures of monoglycerides of fatty acids having a total monoesters content of at least 51% where the monoesters are those with from 10–20 carbon atoms. Diglycerides and triglycerides of fatty acids, or mixtures thereof, are also included. Fatty acids are, for example, lauric acid, myristic acid, stearic acid, oleic acid, linoleic acid and palmitic acid. Monoglyceride permeation enhancers include glyceral monooleate, glycerol monolaurate and glycerol monolinoleate, for example. In a preferred embodiment, the permeation enhancer is a polyethelene glycol-3-lauramide (PEG-3LR), glycerol monooleate (GMO), glycerol monolinoleate or glycerol monolaurate (GML), more preferably, glycerol monooleate. Other preferred permeation enhancers include, but are not limited to; diethylene glycol monoethyl ether, dodecyl acetate, propylene glycol, methyl laurate, ethyl acetate, isopropyl myristrate, ethyl palmitate, isopropyl palmitate glycerol monocaprylate isopropyl oleate, ethyl oleate, lauryl pidolate, lauryl lactate, propylene glycol monolaurate, n-decyl methyl sulfucide.

The multi-zone test systems can use various indicating reagent technologies including: indicating dyes and an antioxidant system to provide threshold readings which can be utilized in multizone nonmetered test formats as described above; indicating dyes which are consumed by the reaction, i.e. a test zone with more dye will turn off at higher concentrations of analyte than a test zone with less dye; and indicating dyes which are generated in proportion to the concentration of an analyte, which may be used in a color match system or in conjunction with a meter such as a spectrophotometer.

A three level sample device can be used in the present invention based on the chemistry systems described below.

| Test Zone | Dye same amount each test area | Antioxidant for damping + antioxidant for creating the level discrimination | Indicating dye + antioxidant for damping + increase concentration for each test area |
|---|---|---|---|
| Low | Color match | Dye + damping antioxidant | Dye + damping antioxidant |
| Medium | Color match | Dye + damping antioxidant and indicating antioxidant | Dye + damping antioxidant + additional |
| High | Color match | Dye + damping antioxidant + more indicating antioxidant than the medium test zone | Dye + damping antioxidant + additional dye + additional dye |

The indicator reagents, oxidase enzymes, peroxidase enzymes, buffers, and antioxidants together with the dye system are impregnated in a membrane matrix selected from polyethersulfone, polysulfone, polyamide, and cellulose.

An alternate means of utilizing the antioxidant damping system is to apply the damping antioxidant solution to a separate absorbent layer which is placed in primary communication with the skin. The indicating reagents and secondary antioxidant reagent is placed in a second absorbent layer in communication with the first layer. This embodiment provides a secondary barrier which prevents the indicating reagent from being transferred back into the patient.

The various aspects of the invention disclosed herein are further illustrated in reference to the following drawings and descriptions thereof.

FIGS. 1–4 show a first embodiment of a patch device 1 according to the present invention.

According to the invention, a frame or support member 2 includes six result zones and a mask 3. The result zones include five test zones 10 and one reaction complete timer 11. Exemplary reaction complete timers are described in U.S. Pat. No. 5,843,691.

The device 1 which includes an embossed matrix 5 having isolated reaction or test zones 10. The device 1 utilizes a porous matrix member 5 having a test side 30 and a absorbent side 31. Preferably, the matrix member 5 is attached to the mask 3 by an adhesive layer 21 which contains openings 23 which correspond to the result zones. The matrix member 5 is preferably an intrinsically hydrophilic material and is optionally impregnated or coated with reagents to facilitate testing. A sample of body fluid is absorbed in the matrix member 5 from the absorbent side 31. The body fluid then wicks to the test side 30 where the body fluid interacts with the testing reagents to create a spectrophotometric change.

The matrix member 5 and mask 3 are fitted within the frame or support member 2. A second adhesive layer 33 is located adjacent the absorbent side 31 of the matrix member 5 and preferably overlaps matrix member 5. A skin interface layer 7 is located next to the second adhesive layer 33 and includes skin permeation enhancers at locations 8. The skin permeation enhancers preferably protrude through openings 34 in the second adhesive layer 33. A third adhesive layer 6 secures the device to a test area and is protected by a guard 9.

As previously noted, the permeation enhancers can comprise chemical means, mechanical means, or one or more combinations thereof.

Indicator reagents are present in the matrix member 5, as well as enzymes, buffers, antioxidants and chelators, which are useful in providing a test device which is capable of determining the level of an analyte in the body fluid sample. The various indicator reagents are known in the art and are conventionally formulated into reagent cocktails with solvents and applied to the matrix member 5. The reagent cocktails for each analyte to be detected are formulated into groups which can coexist at the same pH and solvent solution conditions. When the body fluid sample wets the absorbent side 31 of the matrix member 5, the reagent present in the matrix member 5, the indicator in the test side 30 of the matrix changes color to provide the desired indication of the analyte, e.g., glucose, in the sample.

The assembly of the first embodiment or device according to the present invention is shown schematically in FIG. 3. The mask 3 is preferably covered by adhesive 21. Openings 25 are punched in the mask 3 to correspond with the test zones 10 and reaction complete timer 11. The matrix 5 is the applied to the mask 3 so that the adhesive 21 adheres to the matrix 5 on the mask 3. The matrix 5 is then embossed into the mask 5 to form uncompressed areas 4 and compressed areas 12.

This composite is then attached to a skin interface layer 7 which is treated with one or more skin permeation enhancers in locations 8 which correspond to the uncompressed areas 4 in the matrix member 12. The mask, adhesive and matrix composite is secured to the skin interface layer 7 by the second adhesive layer 33. The third adhesive layer 6 is attached to the frame 2. The third adhesive layer 6 is adjacent the second adhesive layer 33. The adhesive layer 6 acts to secure the patch or device to the patient's skin. The second adhesive layer 33 preferably overlaps an opening in the third adhesive layer 6 in order to add to the overall thickness of the device 1. The guard 9 protects the adhesive layer 6 and the skin interface layer 7 (which optionally contains an antioxidant) until the patch is applied to the patient's skin. A bottom view of the device with the guard 9 removed showing skin permeation enhancers in locations 8 is shown in FIG. 4.

FIG. 5 shows a cross section of a second embodiment of the device 1' which uses adhesive to segregate the reaction zones 100 without using a mask. Instead, adhesive 102 is imbibed into the matrix 104 to form a hydrophobic barrier which forms reaction zones 100. Otherwise the second embodiment is assembled in the same way as the first embodiment.

FIG. 6 shows a sectional view of a third embodiment in accordance with the present invention. The device 1" of the third embodiment includes a matrix gel 200, and an impermeable backing 202, which is transparent so as not to obscure indicator colors. A pocket 204 to hold gel 200 is formed between backing 202 and a semipermeable membrane 206. The semi-permeable membrane 206 is in communication with gel 200 and is secured to the impermeable backing 202 by heat sealing the membrane 206 and the backing 202 together at their periphery. Multiple pockets may be formed by heat sealing the membrane 206 and backing 202 together to segregate one pocket from another. An absorption side matrix 208 is in communication with semipermeable membrane 206 and acts to wick interstitial body fluid toward the gel matrix 200. A contact adhesive 210 applied to the semipermeable membrane 206 is protected by a release liner 212.

Once the release liner 212 is removed, the adhesive is connected to a skin compromising system such as those discussed earlier (e.g., a sheet of tiny tines). The adhesive 210 is semipermeable to allow interstitial body fluid pass through the adhesive 210 and ultimately into the gel matrix 200.

Advantages of the embodiment shown in FIG. 6 include the safe containment of potentially harmful components of the indicating reagent in the test side matrix and improved adhesion or contact between the patch and skin surface. The strips can either be heat sealed or bonded using hot melt or pressure sensitive adhesive material.

In addition, the matrix gel 200 preferably includes an osmotic agent (NaCl) along with indicator reagents to greatly improve the kinetics of interstitial fluid flow. Using this system greatly improves the flow rate of interstitial fluid over the flow rates obtained through the use of skin permeation enhancing means such as chemical adjuvants, electrical potential, ultrasound, mechanical penetration, etc.

The visual glucose test strip is applied to the skin surface following removal of the release liner 212. The skin may be pre-treated chemically, mechanically, ultrasonically, or electrically prior to applying the strip or patch. The interstitial fluid will then migrate through the layers of contact adhesive 210, absorption matrix 208, semipermeable membrane 206 and then into the test matrix gel 200. The indicator dye will then develop color at some preprogrammed temporal sequences and/or glucose concentrations. The transparent impermeable backing 202 keeps the interstitial fluid from rising to the surface of the device. The semi-permeable membrane 206 is permeable to glucose but impermeable to the indicator reagent components. Therefore, the embodiment illustrated in FIG. 6 renders improved safety to users by containing indicator reagent components away from the patient's skin.

In a fourth embodiment shown in FIG. 7, the device 1'" includes an absorbent or wicking layer 75 is placed between the skin interface layer 7 and matrix 5 to dampen out an analyte signal from contaminants. The wicking or absorbent layer 75 is imbibed with antioxidant. An adhesive 76 is imbibed into those areas of the absorbent layer 75 not corresponding to test zones 30 to make it hydrophobic in those areas. The wicking layer 75 preferably made of a non-woven fibrous sheet such as Accuwik®14–12 or Whatman 541. Except for the wicking layer 75, the fourth embodiment can be structurally similar to the first embodiment shown in FIGS. 1–4, thus corresponding features have been labeled using the same reference numerals previously used.

All embodiments of this invention can include skin interface layer 7 having tiny tines to replace skin permeation enhancers in locations 8 to compromise the skin so that body fluid can be extracted through the skin. The literature documents these members such as chemical enhancers, tiny tines to roughen the skin to extract interstitial fluid, reverse iontophores, electroporation, and ultrasonic devices. In addition, all embodiments can be designed to be completely disposable or have a reusable skin compromising system.

Preferably, the matrix material 5 such as illustrated in FIG. 2 will generally by in the ranges of about 3 mils to 30 mils in thickness. (1 mil=0.001 inch=0.0254 mm.) In most test devices a thickness of about 4 to 5 mils is preferred. On the test side 4 of matrix 5, the thickness of the skin will be about 0.5 mil or less. The mask member such as 3 in FIG. 2 will preferably be a polymeric strip having a thickness preferably from about 3 mils to about 12 mils in most applications. However, depending on the type of polymeric strip employed a thickness of about 2 to 4 mils may be more preferred for the mask member. The skin interface layer 7 in FIG. 2 preferably has a thickness of from about 0.5 mils to about 5 mils with about 1 to 2 mils in thickness being most preferred.

Certain members of the devices of this invention which provide fixed volumetric openings into which the matrix material is compressed will preferably be in the range of 4 to 12 mils in thickness and more preferably about 4 to 5 mils in thickness. It will also be recognized that these members providing the volumetric fixed size openings will preferably be injection molder materials but can be sufficiently rigid in noncompressable polymeric strips from which the desired volumetric opening has been punched or dye cut.

It will be recognized by those skilled in the art that the overall thickness of the assembled test strip or patch devices according to the present invention may vary according to the desired use. The overall thickness of the assembled devices preferably range from about 8 to about 40 mils. Due to the strength provided by laminating the various layers, thinner layered materials may be used and provide sufficient strength. However, the overall thickness of a test device according to this invention will be determined also by the necessary and desired thickness of the matrix member to provide color separation and sufficient volume absorption. In addition, the embodiments of this invention providing the fixed volumetric openings will dictate the thickness of the layers providing the volumetric openings of desired volume for the titration tests enabled by the devices of this invention.

When the matrix member is compressed into the adjacent member, the typical matrix material preferably has a thickness of about 5 mils to about 12 mils will preferably be compressed in the compressed area to a thickness of about 1 mil or less and more preferably less than about 0.5 mil. At the same time the portion of the matrix layer which protrudes into the volumetric opening will remain at or near its full original thickness.

The methods of assembling the devices according to the present invention will be apparent to one skilled in the art following the teaching contained herein together with conventional laminating techniques for application of adhesive to the various layers, heat bonding various layers and similar techniques for assembly of the devices disclosed herein.

The devices according to the invention are conveniently made into test patches of convenient size and configuration for individual use. The devices according to the invention are also configured for visual inspection or for use with instruments or meters which are adapted to measure the color or other indicator provided by the test strips. It is desirable to have a system, or kit, which contains all the necessary supplies for performing a test. A kit is particularly advantageous for diabetic patients, many of whom are highly mobile. As mentioned earlier, the patch can be designed to be completely disposable or have a reusable skin compromising system. The presentation of a complete testing kit is also extremely useful for individuals as well as for clinics or visiting nurse groups where complete segregation of all testing supplies from patient to patient is advantageous.

An example of a kit 300 according to the present invention is shown schematically in FIG. 8. Individually foil wrapped patches 302 coupled with an applicator 304 provides the minimum supplies required to perform a glucose test. Preferably, the kit 300 includes a prepackaged towlette 306 to clean and/or numb the test area of the patient's skin and a measuring device or chart 308 to facilitate accurate reading of the color change or other indicators of analyte level in the test patch. Measuring devices are described in U.S. Pat. No. 5,585,790. By grouping all of the necessary components to perform analyte testing together in a kit, proper and consistent use of the test device is encouraged.

The following are examples which further illustrate making and using devices of the present invention.

EXAMPLES

Glucose Test

Example A

Test Reagents

Reagent 1a 40 mg MBTH-S 80 mg DMAB 5 ml acetonitrile and 5 ml water

Stir until all solids are dissolved.

Reagent 2a 6 ml water 10 mg EDTA, disodium salt 200 mg PolyPep, low viscosity (Sigma)

0.668 g sodium citrate 0.2M Aconitic acid buffer 0.5% Polyquart, a binder 2.0 ml 6 wt % Gantrez AN-139 dissolved in water (GAF)

30 mg horseradish peroxidase, 100 units/mg, and 3.0 glucose oxidase, 2000 units/mi Stir until dissolved.

Reagent 3a

Damping antioxidant solution of 50:50 ethanol and ascorbic acid at a pH of 4.0, in varying amounts.

Test A

Polyethersulfone Matrix

A piece of polyethersulfone membrane is uniformly coated with reagent 1a; the excess is squeegeed off and the material is dried. The membrane is then coated with reagent 2a in the same fashion and dried. The antioxidant solution reagent 3a is directly applied to the test areas in varying concentrations using a syringe. The membrane is then assembled into a test device as shown in FIG. 2. The patch is firmly applied to the patients skin opening tiny micro pores in the skin and the glucose level is read from the front based on the indicator response in each of the test zones.

Cellulose Fiber

A piece of cellulose fiber matrix is discretely coated with reagent 1a and dried. It is then discretely coated with reagent 2a and dried. The antioxidant solution reagent 3a is applied to each test area in varying concentrations using a syringe. The membrane is then assembled into a test device as shown in FIG. 2. The device is test similar to the polyethersulfone device.

Test B

Polyethersulfone Matrix

A piece of polyethersulfone membrane is uniformly coated with reagent 1a, the excess is squeegeed off and the material is dried. It is then coated with reagent 2a in the same fashion and dried. The antioxidant solution reagent 3a is applied to the test areas in varying concentrations using a syringe. The membrane is then assembled into a test device as shown in FIGS. 2 and 3. The device is tested similarly to the above test where the highest reacted reaction zone is read.

Cellulose Fiber

A piece of cellulose and glass fiber matrix is discretely coated with reagent 1a and dried. It is then discretely coated with reagent 2a and dried. The antioxidant solution reagent 3a is applied to each test area in varying concentrations using a syringe. The membrane is then assembled into a test device as shown in FIGS. 2 and 3. The device is tested similarly to the above test where the highest reacted reaction zone is read.

The dry chemistry reagent system can be used with the identified membranes in many different ways. The system can be used to develop a visual patch for multiple analytes or for varying concentrations of the same analyte. The system can be used for meter read or color match tests. Additional enhancements can be developed by interfacing the patch with a meter and providing novel interface systems for the test device and meter.

The present invention has been described with reference to preferred embodiments. However, it will be readily apparent to those skilled in the art that it is possible to embody the invention in specific forms other than as described above without departing from the spirit of the invention. The preferred embodiments are illustrative and should not be considered restrictive in any way. The scope of the invention is given by the appended claims, rather than the preceding description, and all variations and equivalents which fall within the range of the claims are intended to be embraced therein.

What is claimed is:

1. A device for determining the presence or concentration of an analyte in the interstitial body fluid of a patient, the device comprising:

(a) a plurality of test areas, each test area independently comprising (i) a porous matrix material having an absorption side and a test side and (ii) an indicating reagent system positioned on or impregnated in the test side of the porous matrix material, wherein each indicating reagent system is capable of indicating the presence or concentration of an analyte in interstitial body fluid by producing a spectrophotometric change upon contact with the interstitial body fluid;

(b) a substantially non-porous material separating each test area from adjacent test areas;

(c) an attachment means for attaching the device to the skin of a patient; and (d) an extraction means for extracting interstitial body fluid through the skin of the patient;

wherein each test area is oriented so that the absorption side of the test area is positioned to contact the interstitial body fluid extracted through the skin of the patient.

2. The device according to claim 1 wherein the porous matrix material is selected from the group consisting of polyethersulfone, polysulfone, polyamide and cellulose.

3. The device according to claim 2 wherein the porous matrix material is polyethersulfone.

4. The device according to claim 3 wherein the porous matrix material has a microporous skin structure on one side and is isotropic through the remaining thickness of the material.

5. The device according to claim 2 wherein the porous matrix material is cellulose fiber.

6. The device according to claim 1 wherein the substantially non-porous material is selected from the group consisting of hot melt adhesives, silicone, fluorocarbon coatings, compressed polyethersulfone membrane, compressed cellulose fiber and combinations thereof.

7. The device according to claim 1 wherein the indicating reagent system comprises (i) an indicator or mixture of indicators capable of undergoing a color change in the presence of an oxidizing agent, and (ii) an oxidase enzyme or a peroxidase enzyme or a mixture thereof.

8. The device according to claim 7 wherein the oxidase enzyme is selected from the group consisting of glucose oxidase, cholesterol oxidase, uricase, alcohol oxidase, aldehyde oxidase and glycerophosphate oxidase.

9. The device according to claim 8 wherein the oxidase enzyme is glucose oxidase.

10. The device according to claim 7 wherein the indicator or mixture of indicators is selected from the group consisting of 2,2'-azino-di(3-ethylbenzthiazoline)sulfonic acid; pyrogallol red; bromopyrogallol red; acid green 25; 4-aminoantipyrene and 5-oxo-1-(p-sulfophenyl)-2-pyrazoline-3-carboxylic acid; 4-aminoantipyrene and N-(m-tolyl)diethanolamine; 4-aminoantipyrene and 4-methoxynaphthol; 3-methyl-2-benzothiazolinone hydrazone hydrochloride and 3,3-dimethylaminobenzoic acid; 3-methyl-2-benzothiazolinone hydrazone hydrochloride and 3,5-dichloro-2-hydroxybenzenesulfonic acid; 3-methyl-2-benzothiazolinone hydrazone hydrochloride and 8-anilino-1-naphthalenesulfonate; 3-methyl-2-benzothiazolinone hydrazone hydrochloride and N-(3-sulfopropyl)aniline; 3-methyl-6-(M sulfonate)-benzothiazolinone-2-hydrazone and 3,3-dimethylaminobenzoic acid; 3-methyl-6-(M sulfonate)-benzothiazolinone-2-hydrazone and 8-anilino-1-naphthalenesulfonate; 3-methyl-6-(M sulfonate)-benzothiazolinone-2-hydrazone and N-(3-sulfopropyl)aniline; and 3-methyl-6-(M sulfonate)-benzothiazolinone-2-hydrazone and N-ethyl-N-(3-sulfopropyl)aniline, where M is sodium, potassium or ammonium.

11. The device according to claim 10 wherein the indicator or mixture of indicators is 3-methyl-6-(M sulfonate)-benzothiazolinone-2-hydrazone, where M is sodium, potassium or ammonium, and N-ethyl-N-(3-sulfopropyl)aniline or N-(3-sulfopropyl)aniline or a mixture thereof.

12. The device according to claim 1 wherein the attachment means comprises an adhesive.

13. The device according to claim 1 wherein the extraction means comprises a skin permeation enhancer or a mixture of skin permeation enhancers; ultrasound; iontophoresis; tape stripping; microtines; electroporation or a combination thereof.

14. The device according to claim 13 wherein the extraction means comprises a skin permeation enhancer or a mixture of skin permeation enhancers; ultrasound; or a combination thereof.

15. The device according to claim 14 wherein the skin permeation enhancer is a glucose permeation enhancer.

16. The device according to claim 14 wherein the skin permeation enhancer is selected from the group consisting of polyethylene glycol-3-lauramide, glycerol monooleate, glycerol monolinoleate, glycerol monolaurate, diethylene glycol monoethyl ether, dodecyl acetate, propylene glycol, methyl laurate, ethyl acetate, isopropyl myristrate, ethyl palmitate, isopropyl palmitate, glycerol monocaprylate, isopropyl oleate, ethyl oleate, lauryl pidolate, lauryl lactate, propylene glycol monolaurate, n-decyl methyl sulucide and mixtures thereof.

17. The device according to claim 1 wherein the each test area optionally further comprises an antioxidant or mixture of antioxidants.

18. The device according to claim 1 further comprising an absorbent layer comprising (i) a porous matrix material and (ii) an antioxidant or mixture of antioxidants, the absorbent layer being in contact with the absorption side of one or more of the test areas.

19. The device according to claim 17 or 18 wherein the antioxidant is selected from the group consisting of 2,3,4-trihydroxybenzoic acid, gallic acid, propyl gallate, ascorbic acid, isoascorbic acid, 3,4-dihydroxycinnamic acid, 3,4-dihydroxybenzaldehyde and 5,6-diaminouracil.

20. The device according to claim 19 wherein the antioxidant is ascorbic acid.

21. The method according to claim 20 wherein the spectrophotometric change or absence thereof is detected or measured by an instrument.

22. The method according to claim 20 wherein the spectrophotometric change or absence thereof is detected or measured visually.

23. The device according to claim 1, further comprising a reaction complete timer.

24. The device according to claim 1, wherein the plurality of test areas define a plurality of microtitration zones having a constant SV/TRV ratio, wherein SV=the sample volume and TRV=the test reagent volume remaining in the matrix.

25. The device according to claim 1, wherein the plurality of test areas and the non-porous material separating each test area are formed by embossments formed on the porous matrix material.

26. A method for testing the interstitial body fluid of a patient for the presence or concentration of an analyte comprising:

providing a device comprising (a) a plurality of test areas, each test area independently comprising (i) a porous matrix material having an absorption side and a test side and (ii) an indicating reagent system positioned on or impregnated in the test side of the porous matrix material, wherein each indicating reagent system is capable of indicating the presence or concentration of an analyte in interstitial body fluid by producing a spectrophotometric change upon contact with the interstitial body fluid; (b) a substantially non-porous material separating each test area from adjacent test areas; (c) an attachment means for attaching the device to the skin of a patient; and (d) an extraction means for extracting interstitial body fluid through the skin of the patient; wherein each test area is oriented so that the absorption side of the test area is positioned to contact the interstitial body fluid extracted through the skin of the patient;

attaching the device to the skin of a patient;

extracting interstitial body fluid through the skin of the patient and onto the absorption side of the test areas;

detecting or measuring a spectrophotometric change or the absence thereof on the test side of the test areas.

27. The method according to claim 26 wherein the porous matrix material is selected from the group consisting of polyethersulfone, polysulfone, polyamide and cellulose.

28. The method according to claim 27 wherein the porous matrix material is polyethersulfone.

29. The method according to claim 28 wherein the porous matrix material has a microporous skin structure on one side and is isotropic through the remaining thickness of the material.

30. The method according to claim 27 wherein the porous matrix material is cellulose fiber.

31. The method according to claim 26 wherein the substantially non-porous material is selected from the group consisting of hot melt adhesives, silicone, fluorocarbon coatings, compressed polyethersulfone membrane, compressed cellulose fiber and combinations thereof.

32. The method according to claim 26 wherein the indicating reagent system comprises (i) an indicator or mixture of indicators capable of undergoing a color change in the presence of an oxidizing agent, and (ii) an oxidase enzyme or a peroxidase enzyme or a mixture thereof.

33. The method according to claim 32 wherein the oxidase enzyme is selected from the group consisting of glucose oxidase, cholesterol oxidase, uricase, alcohol oxidase, aldehyde oxidase and glycerophosphate oxidase.

34. The method according to claim 33 wherein the oxidase enzyme is glucose oxidase.

35. The method according to claim 32 wherein the indicator or mixture of indicators is selected from the group consisting of 2,2'-azino-di(3-ethylbenzthiazoline)sulfonic acid; pyrogallol red; bromopyrogallol red; acid green 25; 4-aminoantipyrene and 5-oxo-1-(p-sulfophenyl)-2-pyrazoline-3-carboxylic acid; 4-aminoantipyrene and N-(m-tolyl)diethanolamine; 4-aminoantipyrene and 4-methoxynaphthol; 3-methyl-2-benzothiazolinone hydrazone hydrochloride and 3,3-dimethylaminobenzoic acid; 3-methyl-2-benzothiazolinone hydrazone hydrochloride and 3,5-dichloro-2-hydroxybenzenesulfonic acid; 3-methyl-2-benzothiazolinone hydrazone hydrochloride and 8-anilino-1-naphthalenesulfonate; 3-methyl-2-benzothiazolinone hydrazone hydrochloride and N-(3-sulfopropyl)aniline; 3-methyl-6-(M sulfonate)-benzothiazolinone-2-hydrazone and 3,3-dimethylaminobenzoic acid; 3-methyl-6-(M sulfonate)-benzothiazolinone-2-hydrazone and 8-anilino-1-naphthalenesulfonate; 3-methyl-6-(M sulfonate)-benzothiazolinone-2-hydrazone and N-(3-sulfopropyl)aniline; and 3-methyl-6-(M sulfonate)-benzothiazolinone-2-hydrazone and N-ethyl-N-(3-sulfopropyl)aniline, where M is sodium, potassium or ammonium.

36. The method according to claim 35 wherein the indicator or mixture of indicators is 3-methyl-6-(M sulfonate)-benzothiazolinone-2-hydrazone, where M is sodium, potassium or ammonium, and N-ethyl-N-(3-sulfopropyl)aniline or N-(3-sulfopropyl)aniline or a mixture thereof.

37. The method according to claim 36 wherein the attachment means comprises an adhesive.

38. The method according to claim 36 wherein the extraction means comprises a skin permeation enhancer or a mixture of skin permeation enhancers; ultrasound; iontophoresis; tape stripping; microtines; electroporation or a combination thereof.

39. The method according to claim 38 wherein the extraction means comprises a skin permeation enhancer or a mixture of skin permeation enhancers; ultrasound; or a combination thereof.

40. The method according to claim 39 wherein the skin permeation enhancer is a glucose permeation enhancer.

41. The method according to claim 39 wherein the skin permeation enhancer is selected from the group consisting of polyethylene glycol-3-lauramide, glycerol monooleate, glycerol monolinoleate, glycerol monolaurate, diethylene glycol monoethyl ether, dodecyl acetate, propylene glycol, methyl laurate, ethyl acetate, isopropyl myristrate, ethyl palmitate, isopropyl palmitate, glycerol monocaprylate, isopropyl oleate, ethyl oleate, lauryl pidolate, lauryl lactate, propylene glycol monolaurate, n-decyl methyl sulucide and mixtures thereof.

42. The method according to claim 36 wherein each test area further comprises an antioxidant or mixture of antioxidants.

43. The method according to claim 36 further comprising an absorbent layer comprising (i) a porous matrix material and (ii) an antioxidant or mixture of antioxidants, the absorbent layer being in contact with the absorption side of one or more of the test areas.

44. The method according to claim 42 or 43 wherein the antioxidant is selected from the group consisting of 2,3,4-trihydroxybenzoic acid, gallic acid, propyl gallate, ascorbic acid, isoascorbic acid, 3,4-dihydroxycinnamic acid, 3,4-dihydroxybenzaldehyde and 5,6-diaminouracil.

45. The device according to claim 44 wherein the antioxidant is ascorbic acid.

46. The method according to claim 26, further comprising providing the device with a reaction complete timer.

47. The method according to claim 26, further comprising defining a plurality of microtitration zones defined by the plurality of test areas, the plurality of microtitration zones having a constant SV/TRV ratio, where SV=the sample volume, any TRV=the test reagent volume remaining in the matrix.

48. The method according to claim 26, further comprising providing the plurality of test areas and non-porous material separating the test areas by embossing the porous matrix material.

49. A process for preparing a device for determining the presence or concentration of an analyte in the interstitial body fluid of a patient, the device comprising: (a) a plurality of test areas, each test area independently comprising (i) a porous matrix material having an absorption side and a test side and (ii) an indicating reagent system positioned on or impregnated in the test side of the porous matrix material, wherein each indicating reagent system is capable of indicating the presence or concentration of an analyte in interstitial body fluid by producing a spectrophotometric change upon contact with the interstitial body fluid; (b) a substantially non-porous material separating each test area from adjacent test areas; (c) an attachment means for attaching the device to the skin of a patient; and (d) an extraction means for extracting interstitial body fluid through the skin of the patient; wherein each test area is oriented so that the absorption side of the test area is positioned to contact the interstitial body fluid extracted through the skin of the patient;

the process comprising the steps of:

providing a porous matrix material having an absorption side and a test side;

applying an indicating reagent system to the test side of the porous matrix material, wherein the indicating reagent system is capable of indicating the presence or concentration of an analyte in interstitial body fluid by producing a spectrophotometric change upon contact with the interstitial body fluid;

compressing a pre-determined portion of the porous matrix material to form a substantially non-porous compressed area and a plurality of uncompressed test areas, each test area comprising the porous matrix material having the indicating reagent system positioned on or impregnated in the test side of the porous matrix material, the substantially non-porous compressed area being located between each test area;

applying or attaching an extraction means for extracting interstitial body fluid through the skin of a patient to the absorption side of the matrix material;

applying or attaching an attachment means for attaching the device to the skin of the patient to form the device.

50. The process of claim 49, wherein the process further comprises applying a substantially non-porous material between each test area.

51. A process for preparing a device for determining the presence or concentration of an analyte in the interstitial body fluid of a patient, the device comprising: (a) a plurality of test areas, each test area independently comprising (i) a porous matrix material having an absorption side and a test side and (ii) an indicating reagent system positioned on or impregnated in the test side of the porous matrix material, wherein each indicating reagent system is capable of indicating the presence or concentration of an analyte in interstitial body fluid by producing a spectrophotometric change upon contact with the interstitial body fluid; (b) a substantially non-porous material separating each test area from adjacent test areas; (c) an attachment means for attaching the device to the skin of a patient; and (d) an extraction means for extracting interstitial body fluid through the skin of the patient; wherein each test area is oriented so that the absorption side of the test area is positioned to contact the interstitial body fluid extracted through the skin of the patient;

the process comprising the steps of:

providing a porous matrix material having an absorption side and a test side;

compressing a pre-determined portion of the porous matrix material to form a substantially non-porous compressed area and a plurality of uncompressed test areas, the substantially non-porous compressed area being located between each test area;

applying an indicating reagent system to the test side of each test area, wherein each indicating reagent system is capable of indicating the presence or concentration of an analyte in interstitial body fluid by producing a spectrophotometric change upon contact with the interstitial body fluid;

applying or attaching an extraction means for extracting interstitial body fluid through the skin of a patient to the absorption side of the matrix material;

applying or attaching an attachment means for attaching the device to the skin of the patient to form the device.

52. The process of claim 51, wherein the process further comprises applying a substantially non-porous material between each test area.

53. A kit for use by a patient to determine the presence or concentration of an analyte in the interstitial body fluid of the patient, the kit comprising:

(1) a device comprising: (a) a plurality of test areas, each test area independently comprising (i) a porous matrix material having an absorption side and a test side and (ii) an indicating reagent system positioned on or impregnated in the test side of the porous matrix material, wherein each indicating reagent system is capable of indicating the presence or concentration of an analyte in interstitial body fluid by producing a spectrophotometric change upon contact with the interstitial body fluid; (b) a substantially non-porous material separating each test area from adjacent test areas; (c) an attachment means for attaching the device to the skin of a patient; and (d) an extraction means for extracting interstitial body fluid through the skin of the patient; wherein each test area is oriented so that the absorption side of the test area is positioned to contact the interstitial body fluid extracted through the skin of the patient;

(2) an applicator for positioning and placing the device on the skin of the patient.

54. The kit according to claim 53 wherein the kit further comprises an applicator for applying at least one of an antiseptic agent and an anaesthetic agent to the skin of the patient.

55. The kit according to claim 53 wherein the kit further comprises a testing device capable converting a spectrophotometric change into an indication of the presence or concentration of an analyte in interstitial fluid.

56. A device for determining the presence or concentration of an analyte in the interstitial body fluid of a patient, the device comprising:

a substantially impermeable backing;

a semipermeable membrane secured to the backing to form at least one pocket;

a gel including an indicator reagent capable of indicating the presence of an analyte in interstitial body fluid by producing a spectrophotometric change upon contact with the interstitial body fluid;

an absorption side matrix in communication with the semipermeable membrane; and an adhesive located on the absorption side of the matrix, the adhesive capable of securing a device to a patient.

57. The device of claim 56 further comprising a release liner covering the adhesive.

58. The device of claim 56 further comprising a skin compromising system attachable to the adhesive layer.

59. The device of claim 56 wherein the gel includes an osmotic agent.

60. The device of claim 59 wherein the osmotic agent is NaCl.

61. The device of claim 56 wherein the absorption side matrix is a non-woven fibrous layer.

* * * * *